(12) United States Patent
Chou et al.

(10) Patent No.: US 6,596,310 B1
(45) Date of Patent: Jul. 22, 2003

(54) METHOD OF ARTIFICIAL INSEMINATION BY TIMED RELEASE OF SPERM FROM CAPSULES OR SOLID BEADS

(75) Inventors: Kuo-Chuan Karen Chou, Okemos, MI (US); Henry Y. Wang, Ann Arbor, MI (US)

(73) Assignees: Board of Trustees operating Michigan State University, East Lansing, MI (US); University of Michigan, Ann Arbor, MI (US)

( * ) Notice: Subject to any disclaimer, the term of this patent is extended or adjusted under 35 U.S.C. 154(b) by 0 days.

(21) Appl. No.: 09/644,483

(22) Filed: Aug. 23, 2000

(51) Int. Cl.[7] .......................... A61K 9/52; A61K 35/52; C12N 11/10; C12N 11/04
(52) U.S. Cl. ...................... 424/457; 424/489; 424/93.7; 424/561; 424/811; 435/2; 435/178; 435/182
(58) Field of Search ............................ 435/2, 174, 178, 435/180, 182; 424/457, 489, 93.7, 561, 811

(56) References Cited

U.S. PATENT DOCUMENTS

| | | | |
|---|---|---|---|
| 5,084,350 A | 1/1992 | Chang et al. | 428/402.2 |
| RE34,326 E | 7/1993 | van Blerkom | 435/2 |
| 5,427,935 A | 6/1995 | Wang et al. | 435/178 |
| 5,451,411 A | 9/1995 | Gombotz et al. | 424/499 |
| 5,744,337 A | 4/1998 | Price et al. | 438/178 |
| 5,834,225 A | 11/1998 | Chou et al. | 435/14 |
| 5,846,530 A | 12/1998 | Soon-Shiong et al. | 424/93.7 |
| 5,912,005 A | 6/1999 | Lanza et al. | 424/424 |

OTHER PUBLICATIONS

Cormier et al., J. Androl. 18:461–468 (1997).
Esbenshade and Nebel, Theriogenology, 33: 499–508 (1990).
Nebel et al., J. Anim. Sci. 60:1631–1639 (1985).
Nebel et al., Reprod. Fertil. Dev. 5:701–712 (1993).
Lin, Ph.D. Dissertation, Michigan State University, East Lansing, MI (1996).
Lin et al., Biol. Reprod. 54, Suppl. 1 (1996).
Weitze, in Boar Semen Preservation II: Proceedings, Second International Conf. on Boar Semen Pres., Supp. to Reprod. in Domestic Animals, Eds: L.A. Johnson and K.F. Weitze, pp. 231–253 (1993).
Pursel et al., J. Animal Sci. 37:528–531 (1973).

*Primary Examiner*—David M. Naff
(74) *Attorney, Agent, or Firm*—Ian C. McLeod

(57) ABSTRACT

A method is provided for encapsulating sperm in a particle wherein the particle provides for the timed release of the sperm. In particular, the method uses a gel forming polymer to form the particle and a medium for maintaining most of the sperm in a non-capacitated stage while it is encapsulated. Further provided is a method for artificial insemination using the encapsulated sperm wherein the sperm is naturally or artificially capacitated after the artificial insemination. In an embodiment, capsules containing a core of sperm in a semen extender are formed as a mixture having membranes of different thicknesses to provide varying time of sperm release. In another embodiment, the sperm and extender are dispersed throughout solid beads that vary in chemical property and diameter to provide varying time of sperm release. The extender may be free of glucose, xanthine oxidase and $H_2O_2$, and contain fructose, fructose-6-phosphate, pyruvate, lactate or mixtures thereof as a carbohydrate source.

13 Claims, 4 Drawing Sheets

METHOD OF ARTIFICIAL INSEMINATION BY TIMED RELEASE OF SPERM FROM CAPSULES OR SOLID BEADS

BACKGROUND OF THE INVENTION

CROSS REFERENCE TO RELATED APPLICATION

None.

STATEMENT REGARDING FEDERALLY SPONSORED RESEARCH OR DEVELOPMENT

None.

(1) Field of the Invention

The present invention relates to an artificial insemination method which comprises providing sperm in a particle wherein the particle provides for the timed release of the sperm. In particular, a method for artificial insemination wherein the sperm in the particle is naturally or artificially capacitated after the artificial insemination. The present invention further relates to a method for encapsulating the sperm in particles and to the particles comprising sperm. In particular, the present invention relates to methods and particles wherein the sperm is provided in a semen extender that provides an energy source which does not facilitate capacitation of the sperm while in the particle. In a preferred embodiment, the particle comprising the sperm is a capsule or a bead.

(2) Description of Related Art

There is increasing demand for genetic transfer and using stored semen for artificial insemination as a means for genetically selecting animals with desirable traits such as production efficiency and meat quality. This demand has prompted a search for methods of storing semen that abrogates the decrease in viability of semen which occurs under prolonged storage. For example, the fertilizing ability of boar semen decreases during storage. Fertility of boar semen stored in liquid at 64° F. in presently available extenders decreases from day one and is substantially diminished after 5 to 7 days. Thus, the farrowing percentages of sows inseminated artificially with semen after 5 days in storage are about half of the farrowing percentages of sows inseminated on the day of semen collection. The limited shelf life of boar semen not only restricts the shipping of semen samples to distant farms but also demands frequent deliveries, thus, the cost of artificial insemination is increased.

Another inherent problem of artificial insemination is the lack of a reliable method for determining the time of ovulation. Heat (standing estrus) detection allows the stockman to estimate when ovulation may occur. Females may be sexually receptive for 1–3 days, depending upon their age and previous experience. The natural estrous cycle in swine varies from individual to individual and ranges from 17 to 25 days. In addition, some sows may ovulate 12 to 24 hours before standing estrus; others may not ovulate until after estrus is detected. This inconsistent timing of ovulation in relation to standing heat further adds to the difficulties in determining when a sow should be inseminated. It is currently recommended that females be inseminated two or three times to compensate for inaccurate heat detection and variations in the timing of ovulation in relation to heat detection.

Currently, the most common method for storing semen is cryopreservation. However, thawing semen that has been frozen generally results in sperm damage.

Furthermore, cryopreservation also causes premature capacitation, which has been proven in bovine spermatozoa, thus, decreasing fertilization ability of the sperm (Cormier et al. J. Androl. 18: 461–468 (1997)). Therefore, there have been attempts to find other means for storing semen or for more effectively cryoprotecting the sperm.

Encapsulation of cells involving the polymerization of polyelectrolytes by multivalent ions is one of the most common methods for immobilizing whole cells. The first example of immobilizing a whole cell by this method was reported by Hackel et al. (Eur. J. Appl. Microbiol. 1: 291–293 (1975)). Currently, whole cell immobilization often uses ionically cross-linked alginate because it is considered non-toxic, economical, and simple to perform. Furthermore, alginate capsules can be coated with polylysine to increase the mechanical stability of the capsules.

U.S. Pat. No. 5,744,337 to Price et al. teaches using alginate to produce microspheres of controllable size in a method that involves internally controlling gelation of alginate in an oil:water emulsion. The method has been used to produce microspheres containing whole cells. The method allows the production of uniform spherical capsules less than 1,000 microns in diameter.

U.S. Pat. No. 5,912,005 to Lanza et al. teaches a method for implanting cells in a host using cells encapsulated in a temperature independent gel. The method uses ionically cross-linked alginate as the encapsulating material; however, to avoid having to use immunosuppressive chemicals to prevent host immune responses to the implanted capsules, the capsules are not coated with polylysine.

U.S. Pat. No. 5,846,530 to Soon-Shiong et al. teaches a method for encapsulating cells for transplantation wherein to strengthen the capsule, the polymer is covalently cross-linked. The covalently cross-linked capsules remain intact in the host for a longer period of time than tonically cross-linked capsules. The patent teaches covalently cross-linking lipids, polysaccharides such as alginate, and polycations to form capsules containing cells.

U.S. Pat. No. 5,084,350 to Chang et al. teaches a method for encapsulating cells consisting of encapsulating the cells in an ionically cross-linked alginate capsule, suspending the capsules in a solution and forming droplets containing one or more capsules, gelling the droplets, forming membranes on the droplets consisting of tonically cross-linked polylysine, and then liquefying the internal alginate capsules. The end product is a cross-linked polylysine capsule containing cells. The method prevents production of capsules containing cells that are trapped within the membrane.

U.S. Pat. No. 5,451,411 to Gumbotz et al. teaches using alginate capsules containing selected polyanions such as polyacrylic acid to shield the therapeutic agent therein from interaction with the alginate. For use in the host, the capsules are treated prior to use with an acid to reduce the molecular weight of the alginate and to prevent its interaction with the therapeutic agent.

Alginate has been used to encapsulate sperm cells. For example, Esbenshade and Nebel (Theriogenology, 33: 499–508 (1990)) encapsulated boar semen in capsules consisting of alginate capsules coated with polylysine. However, they found that the encapsulation caused an accelerated decrease in motility of the boar sperm. There was a complete loss of motility by 16 hours after encapsulation. The fertilizibility of the sperm was not evaluated. In another example, Nebel et al. (J. Anim. Sci. 60: 1631–1639 (1985)) encapsulated bovine sperm in polylysine coated alginate capsules; however, the sperm showed diminished motility and complete loss of fertility after encapsulation. In an effort to reduce spermatozoal injury of encapsulated sperm, Nebel et al. (Reprod. Fertil. Dev. 5: 701–712 (1993)) encapsulated sperm in polymers consisting of polylysine, polyvinylamine or protamine sulfate. The encapsulated sperm was capable of fertilization, but the encapsulated sperm were at a disadvantage to non-encapsulated sperm when cows were inseminated at conventional times.

Another approach to encapsulating sperm was the use of a thermal gel, wherein the thermal gel was solid at room temperature and liquid at body temperature. U.S. Pat. No. RE34,326 to van Blerkom teaches a method for encapsulating sperm for artificial insemination in nontoxic polymers such as polyurethane-polyether polymers which are freely flowing at body temperature and a gel or solid at room temperature. Bovine sperm encapsulated in the polymer and stored for 14 days at 7° C. retained about 48% of its motility. Fertility of the sperm was not determined.

Therefore, while the prior art has taught methods for encapsulating semen, the prior art has not provided a proven means for prolonging the shelf life of liquid semen or reducing the damage to frozen semen. Thus, there remains a need to prolong the shelf life of semen, particularly the shelf life of boar semen. There is also a need for a method to extend the fertile period of the sperm cells in the female reproductive tract. Prolonging the shelf life of the semen would decrease the cost of the semen and the costs for shipping, it would improve the breeding efficiency by increasing the number of females settled by artificial insemination, it would decrease the labor involved in artificial insemination by reducing the number of times artificial insemination needed to be performed to achieve maximum pregnancy, and it would improve overall artificial insemination management because the variation in the timing of ovulation becomes less critical for successful artificial insemination.

SUMMARY OF THE INVENTION

The present invention comprises a method for encapsulating sperm within a particle comprising the steps of: (a) providing a sperm sample comprising a semen extender which provides an energy source that does not facilitate capacitation of the sperm and a gel forming polymer; (b) forming the sperm sample into a droplet containing the sperm sample; and (c) forming the particle by inducing the gel forming polymer to gel. Preferably, the semen extender is substantially free of glucose and reactive oxygen species and provides an exogenous energy source which does not facilitate capacitation of the sperm in the absence of the reactive oxygen species or the glucose. Preferred exogenous energy sources include those selected from the group consisting of fructose, fructose-6-phosphate, pyruvate, lactate, and mixture thereof.

In a particular method of the invention, the particle is a capsule comprising the sperm sample encapsulated by a membrane comprising the gel forming polymer wherein the gel forming polymer, preferably an ionotropic polymer, is induced to gel by a polyvalent ion. The gel forming polymer can be selected from the group consisting of sodium alginate, chitosan, guar gum, gum arabic, carrageenan, pectin, gelatin, iragacanth gum, xanthan gum, and mixture thereof.

In another method of the invention, the particle is a bead comprising the sperm sample encapsulated in a thermal gel that is a solid at room temperature and a liquid at body temperature. Preferred thermal gels include those selected from the group consisting of agarose, kappa-carrageenan, gelatin, agar, polyurethane-polyether polymers, and mixture thereof.

The present invention also provides several particular methods for encapsulating sperm within a capsule. The first method comprises the steps of (a) providing a sperm sample which is in a semen extender and a gelling inducer; (b) forming the sperm sample into a droplet containing the sperm sample, the droplet having an outer surface; (c) providing a gelling solution comprising an effective amount of a gel forming polymer which polymer gels on contact with the gelling inducer at the outer surface of the droplet; and (d) forming a capsule including an interior core and a gel membrane by contacting the outer surface of the droplet with the gelling solution for a time sufficient for the gel forming polymer to form a gel membrane at the surface of the droplet to a desired thickness, the core containing the sperm sample.

A second method for providing sperm within a bead comprises the steps of (a) providing a sperm sample which is in a semen extender and a gel forming polymer; (b) forming the sperm sample into a droplet containing the sperm sample; (c) providing a gel inducing solution comprising an effective amount of an inducer which causes the gel forming polymer to gel on contact with the gelling inducer; and (d) forming a bead by contacting the droplet with the gel inducing solution for a time sufficient for the gel forming polymer to form a gel to provide the sperm sample in the bead.

In either method, it is preferable that the semen extender is substantially free of glucose and reactive oxygen species and provides an exogenous energy source which does not facilitate capacitation of the sperm in the absence of the reactive oxygen species or the glucose. In particular, wherein the exogenous energy source is selected from the group consisting of fructose, fructose-6-phosphate, pyruvate, lactate, and mixture thereof.

It is further preferable that the gel forming polymer be an ionotropic polymer and the gel inducer is a polyvalent ion. In particular, the polymer is selected from the group consisting of sodium alginate, chitosan, guar gum, gum arabic, carrageenan, pectin, gelatin, iragacanth gum, xanthan gum, and mixture thereof.

The present invention further provides a method for encapsulating sperm within a thermal gel membrane capsule comprising the steps of (a) providing a sperm sample which is in a semen extender and a gelling inducer; (b) forming the sperm sample into a droplet containing the sperm sample, the droplet having an outer surface; (c) providing a gelling solution comprising an effective amount of a gel forming polymer which polymer gels on contact with the gelling inducer at the outer surface portion of the droplet and a thermal gel forming polymer at a temperature sufficient to inhibit the gel forming polymer from gelling; (d) forming a capsule including an interior core and a gel membrane by contacting the outer surface of the droplet with the gelling solution for a time sufficient for the gel forming polymer to form a gel membrane at the surface of the droplet to a desired thickness, the core containing the sperm sample, and the membrane entrapping the thermal gel forming polymer; and (e) removing the gel forming polymer to produce the thermal gel membrane capsule.

Further still, the present invention provides a method for encapsulating the sperm in a thermal gel bead, the method comprising the steps of (a) providing a sperm sample which is in a semen extender containing a thermal gel forming polymer and gelling inducer at a temperature sufficient to inhibit the gel forming polymer from gelling; (b) forming the sperm sample into a droplet containing the sperm sample; (c) providing a gelling solution to lower the temperature; (d) forming a bead by contacting the droplet with the gelling solution for a time sufficient for the gel forming polymer to form a gel; and (e) allowing the thermal gel to solidify to produce the thermal gel bead containing the sperm in the semen extender.

Further still, the present invention provides a method for providing the sperm in a thermal gel bead, the method comprising the steps of (a) providing a sperm sample which is in a semen extender containing a thermal gel forming polymer and a gel forming polymer at a temperature sufficient to inhibit the gel forming polymer from gelling; (b) forming the sperm sample into a droplet containing the sperm sample; (c) providing a gel inducing solution comprising an effective amount of a gel inducer which on contact with the gel forming polymer causes the gel forming polymer to gel; (d) forming a bead by contacting the droplet with the gel inducer solution for a time sufficient for the gel forming polymer to form a gel; and (e) allowing the thermal gel to solidify to produce the thermal gel bead that contains the sperm in the semen extender and the gel forming polymer.

Further still, the present invention provides a method for encapsulating the sperm in a thermal gel bead, comprising the steps of (a) providing a sperm sample which is in a semen extender containing a thermal gel forming polymer at a temperature sufficient to inhibit the gel forming polymer from gelling; (b) forming the sperm sample into a droplet containing the sperm sample; and (c) forming the bead by chilling the droplet to a temperature that is below the gelling temperature of the thermal gel whereby the droplet becomes a solid which contains the sperm in the semen extender.

Preferably in the aforementioned, the semen extender is substantially free of glucose and reactive oxygen species and provides an exogenous energy source which does not facilitate capacitation of the sperm in the absence of the reactive oxygen species or the glucose. Preferred exogenous energy sources include those selected from the group consisting of fructose, fructose-6-phosphate, pyruvate, lactate, and mixture thereof. It is also preferable that the gel forming polymer is induced to gel by a polyvalent ion. Preferably, the gel forming polymer is an ionotropic polymer, which can be selected from the group consisting of sodium alginate, chitosan, guar gum, gum arabic, carrageenan, pectin, gelatin, iragacanth gum, xanthan gum, and mixtures thereof. It is preferable that the thermal gel be a polymer that is a solid at room temperature and a liquid at body temperature. Preferred thermal gels include those selected from the group consisting of agarose, kappa-carrageenan, gelatin, agar, polyurethane-polyether polymers, and mixture thereof.

The present invention further provides a method for artificial insemination comprising (a) providing an admixture of particles containing sperm in a semen extender which provides an energy source that does not facilitate capacitation of the sperm wherein the admixture comprises particles that vary in chemical property and diameter; and (b) introducing the admixture into a uterus. In one embodiment, the method comprises particles that are capsules comprising a core containing the sperm sample in a semen extender and a gel membrane encapsulating the core wherein the admixture comprises capsules having membranes of different thicknesses. In another embodiment, the particles are beads comprising the sperm sample in a semen extender and thermal gel.

Preferably, in the artificial insemination method, the semen extender is substantially free of glucose and reactive oxygen species and provides an exogenous energy source which does not capacitate the sperm in the absence of the reactive oxygen species or the glucose. In particular, wherein the exogenous energy source is selected from the group consisting of fructose, fructose-6-phosphate, pyruvate, lactate, and mixtures thereof and wherein glucose or precursors for reactive oxygen species are delivered with the particles containing the sperm during the artificial insemination. It one embodiment, the particles containing glucose or precursors for reactive oxygen species are delivered with the particles containing the sperm during the artificial insemination. It is preferable that the reactive oxygen species is produced by a mixture of xanthine and xanthine oxidase or $H_2O_2$.

In particular embodiments, the gel forming polymer is a thermal gel. Preferably, a thermal gel selected from the group consisting of agarose, kappa-carrageenan, gelatin, agar, polyurethane-polyether polymers, and mixture thereof.

In embodiments comprising a membrane, it is preferable that the membrane have a thickness from 0.1 to 3.5 mm and containing therein sperm in a semen extender.

In particular embodiments, the gel forming polymer is induced to gel by a polyvalent ion. Preferably, the gel forming polymer is an ionotropic polymer. The polymer can be selected from the group consisting of sodium alginate, chitosan, guar gum, gum arabic, carrageenan, pectin, gelatin, iragacanth gum, xanthan gum, and mixture thereof.

The present invention further provides a particle for the timed release of sperm in a uterus comprising sperm in a semen extender which provides an energy source that does not facilitate capacitation of the sperm and a gel forming polymer which forms the particle.

In one embodiment, the particle is a capsule comprising an inner core containing the sperm in a semen extender and a gel forming polymer membrane encapsulating the core wherein chemical property and thickness of the gel membrane determines the time release of the sperm when the capsule is introduced into the uterus. Preferably, the gel forming polymer is selected from the group consisting of agarose, kappa-carrageenan, gelatin, agar, polyurethane-polyether polymers, sodium alginate, chitosan, guar gum, gum arabic, carrageenan, pectin, iragacanth gum, xanthan gum, and mixture thereof.

In another embodiment, the particle is a bead comprising the sperm in a semen extender and a gel forming polymer wherein chemical property and diameter of the bead determines the time release of the sperm when the bead is introduced into the uterus.

In either embodiment, the semen extender is substantially free of glucose and reactive oxygen species and provides an exogenous energy source which does not facilitate capacitation of the sperm in the absence of the reactive oxygen species or the glucose. It is preferable that the exogenous energy source be selected from the group consisting of fructose, fructose-6-phosphate, pyruvate, lactate, and mixture thereof.

In particular embodiments, the gel forming polymer is selected from the group consisting of agarose, kappa-carrageenan, gelatin, agar, polyurethane-polyether polymers, sodium alginate, chitosan, guar gum, gum arabic, carrageenan, pectin, iragacanth gum, xanthan gum, and mixture thereof. In other embodiments, particularly in the bead embodiment, the gel forming polymer is a thermal gel. Preferably, a thermal gel selected from the group consisting of agarose, kappa-carrageenan, gelatin, agar, polyurethane-polyether polymers, and mixture thereof. In a further embodiment of the bead, the bead is encapsulated in a membrane comprising a gel forming polymer.

OBJECTS

It is an object of the present invention to provide a method for encapsulating sperm in a particle, either a capsule or a bead wherein the sperm is maintained in a precapacitated or non-capacitated form. A further object of the present invention is to provide particles which allow for the timed release of the sperm when the particle is implanted in the uterus.

It is also an object of the present invention to provide a method to prolong the shelf life of semen, particularly the shelf life of boar semen and concomitantly to expand or widen the fertile period of the sperm cells in the female reproductive tract.

These and other objects will become increasingly apparent through the following detailed description of the invention and examples.

DESCRIPTION OF PREFERRED EMBODIMENTS

All patents, patent applications, and literature references cited in this specification are hereby incorporated herein by reference in their entirety. In case of conflict, the present description, including definitions, will control.

The overall objectives of the present invention are to prolong sperm shelf-life in storage, and during artificial insemination, provide sufficient fertile sperm in the female reproductive tract over an expanded period of time. To achieve these results, the present invention has three specific aims, (1) providing a sperm compatible hydrogel to encapsulate the sperm cells, (2) providing a semen extender to maintain sperm cells at a non-capacitated or precapacitated stage, and (3) providing a means to effect the timed release of the sperm in the uterus.

As used herein, the term "ionotropic gel forming polymer" refers to a polymer that in the presence of a gel inducing agent, which is an ion of a charge opposite to the charge of the polymer, forms a gel membrane wherein the inducing agent ions hold the membrane together by forming ionic bridges between adjacent polymer molecules. The gel membrane can be dissociated by removing the gel inducing agent with an ion chelating agent or by replacing the inducing agent with monovalent ions. For example, a solution containing alginate in the presence of calcium forms a calcium-alginate gel membrane. The calcium-alginate membrane can be dissociated by adding EDTA which removes the calcium from the membrane, thereby releasing the ionotropic gel forming polymers.

As used herein, the term "thermal gel forming polymer" refers to polymers which undergo gelation when their temperature is lowered below their gelation temperatures and generally have chemical and mechanical properties which are superior to ionotropic gels. For example, a solution containing 0.5% agarose which has been heated to a temperature that dissolves the polymer will remain a liquid as long as the agarose solution is kept at a temperature above the gelling temperature of the agarose.

As used herein, the term "particle" refers to both capsules and beads for containing the sperm sample and/or an exogenous energy source. In general, the term "capsule" refers to a particle that has a core encapsulated in a membrane which is comprised of a gel forming polymer and/or a thermal gel polymer, and the term "bead" refers to a solid particle which encapsulates the sperm sample wherein the sperm sample is dispersed throughout the particle. The term "encapsulate" is used herein to indicate the sperm sample in the capsule or in the bead.

In nature, each ejaculate contains a mixed population of sperm cells; some become capacitated sooner than others (Lin, Ph.D. Dissertation, Michigan State University, East Lansing, Michigan (1996); Lin et al. Biol. Reprod. 54, Suppl. 1 (1996)). This staggered schedule allows the extended presence of newly capacitated and fertile sperm in the female reproductive tract when the earlier capacitated sperm becomes nonviable and dies.

In practice, it is desirable to use sperm from particular animals to inseminate multiple females, both on the immediate farm and on farms distant from the immediate farm. However, to ship sperm to these other farms, a means for preserving the sperm until it is ready for use is required. Currently, the method used for long term preservation of sperm is cryopreservation, but cryopreservation usually results in damage to cellular membrane, thereby, reducing sperm viability when thawed for use. Furthermore, existing semen extenders cause premature capacitation of sperm and synchronization of capacitation which decreases the fertile period of the sperm. Thus, excessive numbers of sperm cells are used for each insemination to compensate for the loss of viable perm cells. Therefore, it has become desirable to develop a more effective means for preserving sperm.

One means for encapsulating bull sperm using an ionotropic alginate poly-L-lysine polymer matrix was developed by Vischwanath et al., (Theriogenol. 48: 369–376 (1996)). However, encapsulation of the sperm in the ionotropic membrane resulted in an unexpected synchronization of sperm capacitation, thereby decreasing the fertile period of each insemination. Thus, the pregnancy rate on inseminated heifers was decreased unless the insemination took place close to the time of ovulation. Furthermore, when the capsules are introduced into the uterus, they must be accompanied with an ion chelator such as EDTA to break down the membrane. Because the beads used in each insemination break down at about the same time and the capacitation is synchronized, the sperm is available for fertilization for only a short period of time. Therefore, the prior art method does not teach a means for preserving sperm that solves the problem of storage and capacitation.

The present invention resolves these problems by providing a means for preserving the sperm in a particle (capsule or bead) in a storage medium that preserves the fertility of the sperm until the sperm is ready for use. In addition, the present invention provides for the timed release of the sperm from the particle after the particles are introduced into the uterus. The timed release of the sperm is achieved by encapsulating the sperm in membrane capsules wherein the membrane varies in thickness and chemical properties, or in particles, which are beads comprising a thermal gel that is a solid at storage temperatures but which melts at the body temperature of the host. In a preferred embodiment, the capsule membranes comprise a thermal gel and time release is achieved by providing an admixture of particles comprising membranes of varying thicknesses. Therefore, when the admixture of particles are introduced into the uterus, the particles melt; the particles with the thinner membranes will release their sperm sooner than the particles with thicker membranes. In the case of the beads, the beads are provided as an admixture of beads of varying diameters. Thus, with either type of particle, the sperm is provided to the host over a greater time period than is possible with sperm encapsulated in an alginate membrane. Since sperm cells released sooner will die sooner if not engaged in fertilizing the egg, the present invention creates a relay of sperm cells that are released in the female reproductive tract. The present invention ensures an extended fertile period after each insemination, thus, increasing the conception rate. The present invention is useful for both human infertility laboratories and hospitals, and livestock companies.

In the present invention, the sperm is maintained in a non-capacitated or precapacitated state by using a medium containing an energy source that does not support capacitation. Even though the uterus naturally contains glucose, it can be desirable to include the following in the insemination process to enhance the capacitation of the encapsulated sperm. A method for capacitation of sperm is taught in U.S. Pat. No. 5,834,225 ('225) to Chou et al. The '225 patent, in addition to teaching methods for capacitating sperm, teaches that in the absence of a reactive oxygen species, carbohydrates other than glucose generally have a poor ability for capacitating sperm. Therefore, sperm in the presence of fructose, fructose-6-phosphate, pyruvate or lactate is poorly capable of fertilizing mouse gametes, whereas sperm in the presence of glucose or glucose-6-phosphate supports the maximum rate of sperm capacitation and fertilization. When xanthine and xanthine oxidase or $H_2O_2$ are added to the sperm stored in a mixture containing fructose or fructose-6-phosphate, the sperm becomes capacitated. It is the hydrogen peroxide or the combination of xanthine and xanthine oxidase which produces superoxide anions that supports sperm capacitation. Therefore, in a preferred embodiment, the present invention maintains the sperm in a medium containing fructose or fructose-6-phosphate which keeps most of the sperm in an non-capacitated state. During the artificial insemination process, the sperm in the particles can be introduced into the uterus with a medium that contains glucose, or xanthine and xanthine oxidase, or $H_2O_2$, or other reactive oxygen species precursor. Thus, as the particles dissolve or melt, the sperm comes in contact with the glucose or reactive oxygen species, which then capacitates the sperm. Since in one embodiment the particles comprise capsules comprising membranes of varying thickness and in another embodiment the particles comprise beads of varying diameters, the sperm is released at different times. Because the sperm is poorly capacitated prior to release, the effective life of the sperm during the artificial insemination process is extended. In a preferred embodiment, the sperm is maintained in a capsule that has an interior region (core) containing the sperm in a semen extender and which is surrounded with a membrane that is a thermal gel.

The present invention embraces any of the methods for making capsules which are disclosed in the following U.S. Patents. U.S. Pat. No. 5,427,935 to Wang et al. teaches a method for making membrane capsules and a process for encapsulating materials such as cells in semi-permeable membranes. In particular, the inventors teach a method for creating a membrane capsule comprised of a thermal gel membrane surrounding an interior region using a process that will not kill the sperm. U.S. Pat. No. 5,846,530 to Soon-Shiong et al. teaches microcapsules prepared from cross-linkable polysaccharides, polycations and/or lipids. U.S. Pat. No. 5,744,337 to Price et al. teaches an internal gelation method for forming multi-layer microspheres. U.S. Patent No. to Gombotz et al. teaches alginate capsules containing specific cations in the capsule to shield the therapeutic agent from interaction from the alginate. U.S. Pat. No. 5,084,350 to Chang et al. teaches a method for encapsulating cells in capsules without making capsules that have cells trapped in the membrane.

Figure 1:
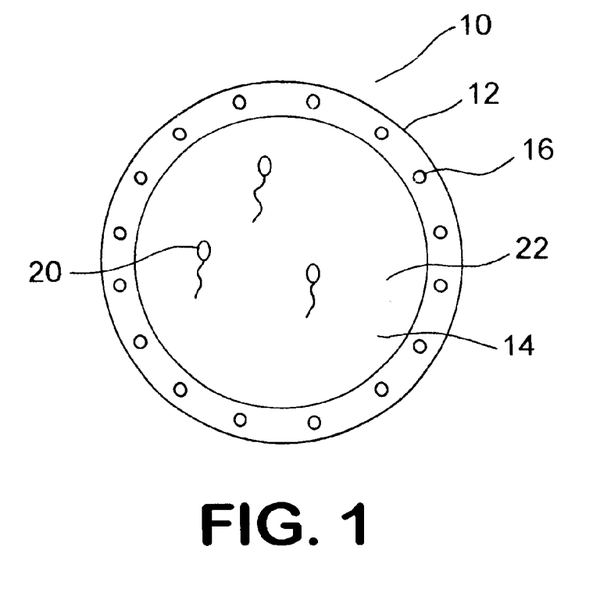
FIG. 1 shows a membrane capsule 10 that consists of a membrane 12 surrounding an interior region 14, which comprises sperm 20 in a precapacitation medium 22 wherein the membrane comprises an ionotropic gel polymer 16.

The particles provided by the present invention are shown in FIGS. 1 through 4. In FIG. 1, the membrane capsule 10 consists of a membrane 12 surrounding an interior region or core 14 which can be liquid. The core 14 comprises sperm 20 in a medium 22, which can provide an energy source that does not facilitate capacitation of the sperm, and the membrane 12 which comprises an ionotropic polymer 16. In FIG. 2A, the membrane capsule 10 consists of a membrane 12 that comprises, in addition to an ionotropic polymer 16, a thermal gel polymer 18. FIG. 2B shows a membrane capsule 10 wherein the membrane 12 comprises a thermal gel polymer 18. FIG. 3A shows a solid bead 30 wherein a solid matrix 32 comprises a medium 22, which can provide an energy source that does not facilitate capacitation of the sperm, sperm 20, and a thermal gel polymer 18 and an ionotropic polymer 16. FIG. 3B shows a solid bead 30 wherein a solid matrix 32 comprises a medium 22, which can provide an energy source that does not facilitate capacitation of the sperm, sperm 20, and a thermal gel polymer 18. FIG. 3C shows a solid bead 30 wherein a solid matrix 32 comprises a medium 22, which can provide an energy source that does not facilitate capacitation of the sperm, sperm 20, and an ionotropic polymer 16. FIG. 4A shows a membrane capsule 10 wherein a solid bead 30 is surrounded by a membrane 12 comprising an ionotropic polymer 16 and a thermal gel polymer 18. FIG. 4B shows a membrane capsule 10 wherein a solid bead 30 is surrounded by a membrane 12 comprising a thermal gel polymer 18. FIG. 4C shows a membrane capsule 10 wherein a solid bead 30 is surrounded by a membrane 12 comprising an ionotropic polymer 16.

Thus, in one embodiment the present invention provides sperm which is maintained in a mostly precapacitated or non-capacitated state in a membrane capsule 10 wherein the membrane 12 varies in thickness and chemical properties.

The thickness of the membrane and chemical properties of the polymer comprising the membrane 12 affects how long it takes for the sperm 20 to be released from the membrane capsule. The thicker the membrane, the longer it takes for the sperm to be released. In one embodiment of the method for making the capsules of the present invention, fresh sperm is placed in a semen extender that provides an energy source that does not facilitate capacitation of the sperm. An example of a semen extender that does not support capacitation is a medium such as M-16 medium modified to contain 5.56 mM fructose or 5.56 mM fructose-6-phosphate. To encapsulate the sperm, a small, effective and diffusible gelling inducer such as $Ca^{2+}$, $K^+$, phosphate, etc. is added. The sperm-gelling inducer medium is made into droplets of sufficient size to contain sperm cells. The droplets can be conveniently made using an atomizer, hypodermic needle, air-jet or other type of sprayer. The droplets are sprayed into a gelling solution comprising an ionotropic gel. The gelling solution contains an effective amount of a gel forming polymer which gels on contact with the gelling inducer. Thus, the drops are encapsulated with a membrane layer. The membrane capsule 10 consists of an inner compartment containing precapacitated sperm 20 and a membrane 12. The thickness of the membrane 12 can be from 0.1 mm to 3.5 mm. The thicker the membrane, the longer it takes for the membrane to be sufficiently dissolved to release the sperm. Therefore, providing a mixture of capsules consisting of sperm encapsulated in membranes of varying thickness to the uterus, results in the differential dissolution of the membranes and thereby effects the release of sperm over an expanded period of time. This timed release of sperm is in contrast to providing the sperm in capsules wherein the capsules all have membranes of the same thickness, which in the uterus would dissolve at the same rate and, thus, release the sperm at the same time. FIG. 1 shows a membrane capsule 10 comprising an ionotropic polymer membrane 12 and a core 14 containing the sperm 20 in a medium 22 which can provide an energy source that does not facilitate capacitation of the sperm. Optionally, the outer surface layer of the membrane 12 can be coated with a second polymer to form a composite membrane.

Figure 2A:
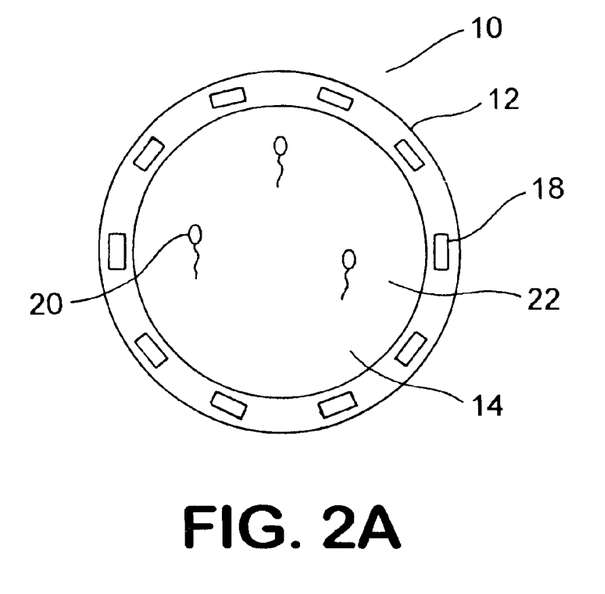
FIG. 2A shows a membrane capsule 10 that consists of a membrane 12 that comprises in addition to the ionotropic polymer 16, a thermal gel polymer 18.
Figure 2B:
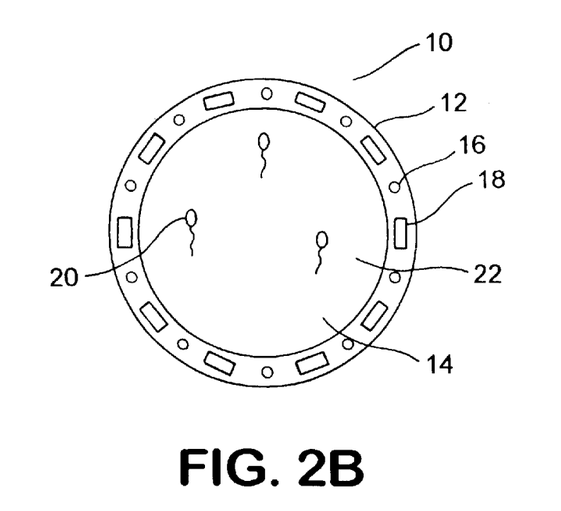
FIG. 2B shows a capsule 10 wherein the membrane 12 comprises a thermal gel polymer 18.

In another embodiment of the present invention, the gelling solution comprises an effective amount of a thermal gel forming polymer in addition to the ionotropic gel forming polymer. The physicochemical conditions can be altered to induce gelling of the second polymer entrapped within the membrane compartment of the capsule. The capsules formed after gelation of the polymer consist of a membrane 12 containing both an ionotropic gel polymer 16 and a thermal gel polymer 18. Optionally, these capsules can be treated with a chelating reagent to remove the ionotropic gel polymer 16, which leaves a membrane consisting of only the thermal gel 18. FIG. 2B shows a membrane capsule 10 with a membrane 12 that consists solely of the thermal gel polymer 18, whereas FIG. 2A shows a membrane capsule 10 with a membrane 12 that consists of an ionotropic gel polymer 16 and a thermal gel polymer 18. In either membrane capsule 10, there is a core 14 which contains sperm 20 in a medium 22 that can be a precapacitation medium that provides an energy source that does not facilitate capacitation of the sperm. Optionally, the outer surface layer of the membrane 12 can be coated with a second polymer to form a composite membrane.

As an example for making the above capsules, semen is first encapsulated in a capsule having a composite calcium alginate-agarose membrane. Then the calcium alginate is removed by treating the capsules with sodium citrate or EDTA, which produces capsules consisting of agarose without the calcium alginate. The capsules can be made having a thickness of 0.1 mm to 3.5 mm. The thicker the membrane, the longer it will take for the capsule to dissolve in the uterus. A mixture of capsules having membranes of different thickness produces a population of capsules that release sperm at different times in the uterus. FIG. 2A shows a thermal gel capsule with an ionotropic gel polymer in the membrane and FIG. 2B shows a thermal gel capsule without the ionotropic gel polymer in the membrane.

In a further embodiment of the present invention, the sperm to be encapsulated is in a medium that optionally provides an energy source that does not facilitate capacitation of the sperm and contains an ionotropic gel polymer. The suspension is then made into droplets of sufficient size to contain sperm cells which are introduced as droplets into a medium containing a small, effective and diffusible gelling inducer such as $Ca^{2+}$, $K^+$, phosphate, etc. The droplets can be conveniently made using an atomizer, hypodermic needle, air-jet or other type of sprayer. The droplets are sprayed into the solution containing the gelling inducer. The droplets containing the sperm gel upon contact; the thickness of the membrane is determined by the length of time the droplet is maintained in the solution containing the gelling inducer. The resulting capsule consists of a membrane comprising the ionotropic polymer which is shown in FIG. 1.

Figure 3A:
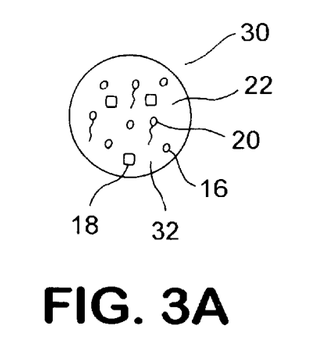
FIG. 3A shows a solid bead 30, which comprises a medium 22 and sperm 20 in a solid matrix 32, which comprises both an ionotropic polymer 16 and a thermal gel polymer 18.
Figure 3B:
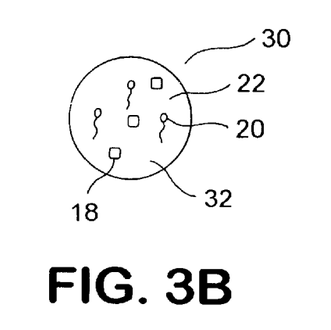
FIG. 3B shows the solid bead 30 wherein the solid matrix 32 comprises a thermal gel polymer 18.
Figure 3C:
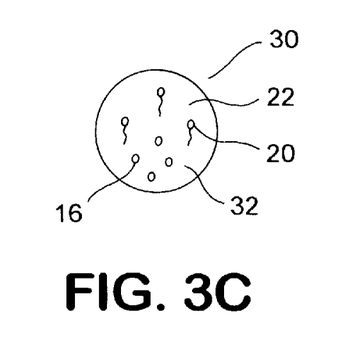
FIG. 3C shows the solid bead 30 wherein the solid matrix 32 comprises an ionotropic polymer 16.
Figure 4A:
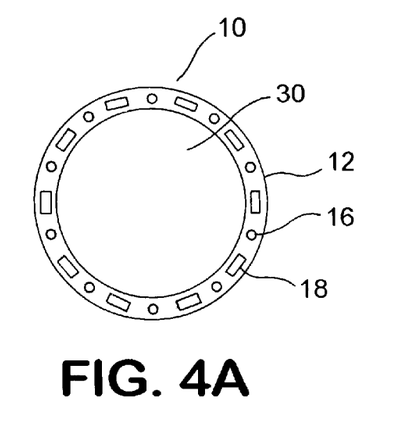
FIG. 4A shows a bead 30 wherein a solid bead 30 is surrounded by a membrane 12 comprising an ionotropic polymer 16 to make a membrane capsule 10.
Figure 4B:
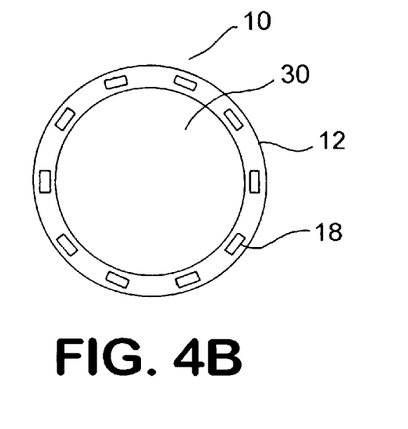
FIG. 4B shows the solid bead 30 surrounded by a membrane 12 comprising a thermal gel polymer 18 to make a membrane capsule 10.
Figure 4C:
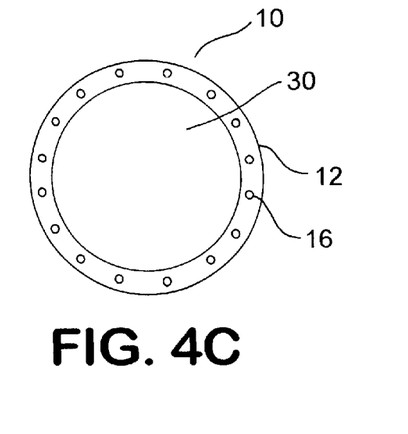
FIG. 4C shows the solid bead 30 surrounded by a membrane 12 comprising an ionotropic polymer 16 and a thermal gel polymer 18 to make a membrane capsule 10.

In an embodiment further still, the sperm to be encapsulated is placed in a medium, which optionally provides an energy source that does not facilitate capacitation of the sperm and contains a mixture of an ionotropic gel forming polymer and a thermal gel forming polymer. Optionally, the mixture is at a temperature that maintains the thermal gel suspension in a liquid state; between about 37° C. to 42° C. The temperature at which the thermal gel suspension is a liquid is an intrinsic property of the thermal gel forming polymers. The suspension is then made into droplets of sufficient size to contain sperm cells, which are introduced as droplets into a medium containing a small, effective and diffusible gelling inducer such as $Ca^{2+}$, $K^+$, phosphate, etc. The droplets can be conveniently made using an atomizer, hypodermic needle, air-jet or other type of sprayer. The droplets are sprayed into the solution containing the gelling inducer. The droplets containing the sperm gel upon contact; the thickness of the membranes is determined by the length of time the droplet is maintained in the solution containing the gelling inducer. Optionally, the ionotropic gel polymer is removed from the capsule using a chelating reagent. In the optional method, the ionotropic gel polymer is removed from the capsule using a chelating reagent, which results in a solid thermal gel capsule containing the sperm. In either case, the resulting particle is a solid bead wherein most of the sperm is maintained in a non-capacitated state. FIG. 3 shows a solid bead 30 made according to the present invention. The bead 30 contains sperm 20 immobilized in the gelled polymer matrix 32 which contains either a thermal gel polymer 18 or ionotropic gel polymer 16 or both and a medium 22 that optionally provides an energy source that does not facilitate capacitation of the sperm 20. Optionally, the bead 30 can be coated with a membrane 12 as shown in FIGS. 4A–C to make a membrane capsule 10, which membrane can consist of a mixture of an ionotropic gel polymer 16 and a thermal gel polymer 18 (FIG. 4A) or solely of a thermal gel polymer 18 (FIG. 4B) or solely of an ionotropic gel polymer 16 (FIG. 4A).

And in a further still embodiment, a thermal gel bead containing sperm is made by forming a suspension comprising the sperm in a medium that contains a thermal gel forming polymer and, which optionally provides an energy source that does not facilitate capacitation of the sperm. The suspension is then made into droplets of sufficient size to contain sperm cells, which are introduced as droplets into a chilling environment that is cold enough to instantly turn the thermal gel to a solid. The droplets can be conveniently made using an atomizer, air-jet or other type of sprayer. The solid bead 30 containing the sperm 20 in a medium 22 in a solid gel matrix 32 is as shown in FIG. 3B and may optionally be coated with a membrane 12 as shown in FIGS. 4A–C, which membrane can consist of a mixture of an ionotropic gel polymer 16 and a thermal gel polymer 18 (FIG. 4A) or solely of a thermal gel polymer 18 (FIG. 4B) or solely of an ionotropic gel polymer 16 (FIG. 4A).

In an optional embodiment of the particles of the present invention, the particles comprise multiple layers of membranes. After the particles are implanted in the uterus, the membrane layers dissolve successively, in a step-wise manner, starting with the outer most membrane. In this manner, sperm is released over an expanded period of time when an admixture of particles consisting of particles with varying numbers of layers is provided. This is in contrast to the prior art wherein sperm is released in a relatively short period of time (for example as disclosed in U.S. Pat. No. RE34,326 to van Blerkom). In an optional embodiment, the sperm is incorporated in either all of the successive membrane layers or in particular membrane layers. Thus, sperm is released as the membrane layers dissociate even though the capsule has not yet become entirely dissociated. In this manner, sperm is continuously released over an expanded period of time. Capacitation is achieved as shown above.

To form particles comprising ionotropic gel polymers, the gelling inducer comprises a polyvalent ion which forms ionic cross-linkages between molecules of the ionotropic gel forming polymer. The ionotropic gel forming polymer can be any non-toxic water soluble gel forming polymer that forms a gel upon contact with a gelling inducer and is compatible with semen such as a water soluble ionotropic gel. The preferred polysaccharides are ionotropic and include, but are not limited to, polysaccharides extracted from vegetable matter such as sodium alginate, chitosan, guar gum, gum arabic, carrageenan, pectin, gelatin, iragacanth gum, xanthan gum and mixture thereof. Upon contact with gel inducers, the polysaccharide molecules form a water insoluble shape-retaining gel membrane capsule. In certain embodiments of the present invention, the gel forming polymer is a thermal gel. A thermal gel forming polymer undergoes gelation when the temperature is lowered below the polymer's gelation temperature. A wide variety of thermal gel forming polymers can be used in the present invention, including, agarose, low-melting temperature agarose, kappa-carrageenan, gelatin, agar, polyurethane-polyether polymers, and mixture thereof. Examples of polyurethane-polyether polymers suitable for encapsulating sperm are disclosed in U.S. Pat. No. RE34,326 to van Blerkom.

The method for encapsulating sperm according to the present invention is suitable for the short-term and long-term storage of sperm. The particle protects the sperm from the environment, and the semen extender maintains the sperm in a non-capacitated stage. The ability to maintain sperm at the non-capacitated stage ensures that the sperm will maintain its fertility for an extended period of time.

The particles of the present invention can also be stored long-term using cryopreservation methods which are well known in the art. For cryopreservation, it is desirable to further include one or more stabilizers with the sperm which helps reduce the formation of ice crystals in the sperm cells and protects the sperm cells from the effects of freezing and thawing the sperm. Examples of stabilizers include dimethylsulfoxide, glycerol, proteins, salts, and carbohydrates.

In the artificial insemination process of the present invention, some of the sperm in the particles can made fertile by capacitation. The uterus naturally contains glucose which will capacitate sperm as they are released from the particles. Thus, for many artificial insemination processes, the particles of the present invention can be used in artificial insemination methods without using exogenous capacitation inducers. However, it can be desirable to induce or enhance capacitation by including particular capacitation inducers with the capsules in the artificial insemination method. For example, capacitation can be facilitated when glucose or 0.125 mM xanthine (X) and 0.0125 units/ml xanthine oxidase (XO) is added to a medium containing the encapsulated sperm prior to insemination. Prior to use, X and XO must be keep separate. When necessary, 34 $\mu$g/ml catalase (C) can be added to selectively remove $H_2O_2$. Afterwards, the particles containing the capacitated sperm are implanted in the uterus. Alternatively, the particles can be implanted in the uterus with a semen extender that provides glucose, or X and XO, or other capacitation inducer, which capacitates the sperm as the sperm is released from the particles. In the case of particles that do not contain an ionotropic gel or are a composite of an ionotropic gel-thermal gel, and which are implanted in the uterus, a preferred extender comprises glucose or 0.125 mM X, 0.125 units/ml XO and 34 $\mu$g/ml C, and optionally 600 IU/ml sodium penicillin G. As the gel melts, the sperm is released and becomes capacitated when it comes in contact with the semen extender. In the case of particles wherein the membrane comprises an ionotropic gel such as alginate, the extender preferably comprises glucose or 0.125 mM X, 0.125 units/ml XO and 0.37% EDTA or other ion chelator, and optionally 34 $\mu$g/ml C and/or 600 IU/ml sodium penicillin G. Inside the uterus, the chelator liquefies the ionotropic gel, which causes the particles to dissolve, thereby releasing the sperm which can become capacitated when it comes in contact with the semen extender. The timed release of sperm is achieved by ionotropic membranes of different chemical properties and thicknesses, or the ionotropic membrane encapsulates a thermal gel membrane, or a thermal gel encapsulates the ionotropic membrane. Capacitating the sperm with glucose is preferred.

In another embodiment, the particles containing the sperm are mixed with a mixture of membrane particles that contain glucose or other capacitation inducers such as precursor reactive oxygen species. When a mixture of the sperm-bearing and glucose or reactive oxygen-bearing capsules are placed into the uterus, the particles release the sperm and glucose or other precursor reactive oxygen species wherein the glucose or reactive oxygen species capacitates the sperm. In a preferred embodiment, the reactive oxygen species is produced by X and XO or $H_2O_2$. Optionally, catalase is provided to control production of an excessive amount of $H_2O_2$ during the reaction. In practice, the X and XO are separately encapsulated to prevent formation of the reactive species until the timed contact with the sperm. Glucose is the preferred means for capacitating the sperm. In a further embodiment, the particles containing the sperm are implanted in the uterus without treatment with glucose or a precursor of a reactive oxygen species. In that case, the capacitation relies upon the glucose naturally present in the uterus.

The following examples are intended to promote a further understanding of the present invention.

EXAMPLE 1

This example illustrates the formation of particles, which are membrane capsules wherein the membrane comprises ionotropic calcium alginate encapsulating a core containing precapacitated sperm.

A sterile solution containing 0.8% calcium alginate, a medium such as M-16 medium containing 5.56 mM fructose is prepared and kept stirred using a magnetic stirrer at room temperature. A sterile suspension containing semen in a modified semen extender consisting of medium such as M-16 medium containing 5.56 mM fructose supplemented with 1.3% $CaCl_2$ (gelling inducer) and 10% dextran (to increase the viscosity of the suspension) is prepared. The suspension is dropped through a hypodermic needle to form droplets which fall into the stirred alginate solution. A capsular membrane forms almost instantaneously around the suspension drop due to the cross-linking of the interfacial alginate molecules by Ca cations. Prior to removal of the membrane capsules, the polymer solution is diluted five-fold by adding the required amount of a modified semen extender. This step dilutes the alginate solution outside the membrane capsules and reduces the possibility of membrane capsules joining each other when they are in close contact, due to gelation of the alginate solution on their exterior surface. The capsules are removed from the solution and excess solution is drained using an appropriate size mesh. The membrane capsules are transferred to a modified semen extender such as M-16 medium containing 1.3% M $CaCl_2$ and incubated for one minute to stabilize the exterior surface. Finally, the membrane capsules are equilibrated with a medium such as M16 medium. Optionally, to strengthen the membrane capsules, the capsules are exposed to a 0.05% poly(L-lysine) solution for 5 minutes.

FIG. 1 illustrates the structure for capsules made according to the above method.

EXAMPLE 2

This example illustrates formation of solid particles, which are beads, containing precapacitated sperm.

A sterile solution containing 0.5% agarose and 0.25% sodium alginate is prepared with a modified semen extender consisting of a medium such as M-16 medium containing 5.56 mM fructose and kept warm using a magnetic stirred using a magnetic stirrer at 37° C. An aqueous suspension containing semen in a modified semen extender consisting of a medium such as M-16 medium containing 5.56 mM fructose and supplemented with 10% dextran to increase the viscosity of the suspension and 1.3% $CaCl_2$ (a gelling inducer) is prepared. The suspension is dropped through a hypodermic needle to form droplets which fall into the alginate/agarose solution. A capsular membrane forms almost instantaneously around the suspension droplet due to the cross-linking of the interfacial alginate molecules by $Ca^{2+}$ cations. The formed membrane particles are equilibrated in a medium such as M-16 medium containing 0.05 M EDTA, which chelates the $Ca^{2+}$ resulting in liquefication of the Ca-alginate in the membrane. Finally, the particles consisting of solely of an agarose membrane are washed and stored in a medium such as M-16 medium. Optionally, the alginate is not removed from the particles.

FIG. 3A illustrates the structure for a solid bead. FIG. 4A illustrates the structure for the optional particle wherein the membrane includes the alginate.

EXAMPLE 3

This example illustrates formation of membrane particles containing membrane particles within.

To make membrane particles containing multiples of the membrane particles, the particles made according to Example 1 or 2 are suspended in an aqueous solution of semen in a modified semen extender consisting of a medium such as M-16 medium containing 5.56 mM fructose and supplemented with 1.3% M $CaCl_2$ and 10% dextran. Drops large enough to contain several particles are dropped through a hypodermic needle as above into a solution containing 0.8% alginate in a modified semen extender consisting of medium such as M-16 medium containing 5.56 mM fructose. The solution containing the particles is immediately encapsulated. The solution is diluted five-fold and the particles are removed and stabilized as above.

Alternatively, drops consisting of particles made according to Example 1 or 2 and containing a gelling inducer are dropped into a solution containing 0.5% agarose and 0.25% alginate as in Example 2. The solution containing the particles is immediately encapsulated. The particles are further processed as in example 2. The alternative process produces particles that are encapsulated within a larger particle.

EXAMPLE 4

This example illustrates formation of gelatin membrane capsules containing precapacitated sperm.

A sterile solution containing 0.5% gelatin and 0.5% sodium alginate is prepared with a modified serum extender consisting of a medium such as M-16 medium containing 5.56 mM fructose is stirred using a magnetic stirrer. An aqueous suspension containing semen in a modified semen extender consisting of a medium such as M-16 medium containing 5.56 mM fructose and supplemented with 10% dextran to increase the viscosity of the suspension and 3.0% $CaCl_2$ (a gelling inducer) is prepared. The suspension is dropped through a large hypodermic needle to form droplets which fall into the alginate/gelatin solution. A capsular membrane forms almost instantaneously around the suspension droplet due to the cross-linking of the interfacial alginate molecules by $Ca^{2+}$ cations. The capsules consisting of an alginate/gelatin membrane are washed and stored. optionally, the formed membrane capsules equilibrated in a medium such as M-16 medium containing 0.05 M EDTA, which chelates the $Ca^{2+}$ resulting in liquefication of the Ca-alginate in the membrane. Finally, the capsules consisting of solely of a gelatin membrane are washed and stored in a medium such as M-16 medium. FIG. 2B illustrates the structure of the above gelatin capsules.

Alternatively, a drop containing multiple capsules made according above are dropped into a solution containing 0.5% gelatin and 0.5% alginate as above. The solution containing the capsules is immediately encapsulated. The capsules are further processed as above. The alternative process produces capsules that are encapsulated within a larger capsule.

EXAMPLE 5

This example illustrates another method for the formation of solid beads containing precapacitated sperm.

A sterile solution containing 0.5% agarose is prepared with a modified semen extender consisting of a medium such as M-16 medium containing 5.56 mM fructose and kept warm using a magnetic stirred using a magnetic stirrer at 37° C. The suspension is dropped through a hypodermic needle to form droplets or sprayed into a chilled atmosphere. The particles solidify forming solid beads.

FIG. 3B illustrates the structure for the above beads.

EXAMPLE 6

This example illustrates in utero implantation of particles made in any one of the Examples.

This example shows that the particles can be implanted in utero using standard artificial insemination techniques. The particles are inseminated into a primiparous sow with a Melrose catheter during the second day of estrus. The particles are introduced with 20 ml of extender containing a capacitation inducer such as 5.56 mM glucose and/or 0.125 mM xanthine, 0.125 units/ml xanthine oxidase and 34 µg/ml catalase. Optionally, sodium penicillin G (600 IU/ml). When the particles are made of alginate, the semen extender also contains 0.37% EDTA.

EXAMPLE 7

This example illustrates the formation of ionotropic calcium alginate membrane particles containing mostly non-capacitated sperm. This example differs from Example 1 because in Example 1 the semen which contains the calcium gelling inducer is added as droplets to the alginate solution to form the particles whereas in this example, the semen which contains the alginate is added as droplets to the calcium gelling inducer solution.

A sterile solution containing in a modified serum extender consisting of a medium such as M-16 medium containing 5.56 mM fructose and 1.3% $CaCl_2$ (gelling inducer) is prepared and kept stirred using a magnetic stirrer at room temperature. A sterile suspension containing semen in a modified semen extender consisting of a medium such as M-16 medium containing 5.56 mM fructose and 0.8% calcium alginate is prepared. The suspension is dropped through a hypodermic needle to form droplets which fall into the stirred solution containing the gelling inducer solution. A capsular membrane forms almost instantaneously around the suspension drop due to the cross-linking of the interfacial alginate molecules by $Ca^{2+}$ cations. Prior to removal of the particles, the gel inducer is diluted five-fold by adding the required amount of medium such as M-16 medium. This step dilutes the gel inducer outside the particles and reduces the possibility of particles joining each other when they are in close contact, due to cross-linking alginate between capsules. The particles are removed from the solution and excess solution is drained using an appropriate size mesh. The particles are transferred to a medium such as M-16 medium containing 1.3% M $CaCl_2$ and incubated for one minute to stabilize the exterior surface. Finally, the particles are equilibrated with a medium such as M-16 medium. Optionally, to strengthen the particles, the particles are exposed to a 0.05% poly(L-lysine) solution for 5 minutes.

FIG. 1 illustrates the structure of the above particles.

EXAMPLE 8

This example illustrates formation of solid particles containing precapacitated sperm. This example differs from Example 2 because in Example 2 the semen which contains the calcium gelling inducer is added as droplets to the alginate-agarose solution to form the capsules whereas in this example, the semen which contains the alginate-agarose is added as droplets to the calcium gelling inducer solution.

A sterile solution containing 1.3% $CaCl_2$ (a gelling inducer) is prepared with a modified serum extender consisting of a medium such as M-16 medium containing 5.56 mM fructose and kept stirred using a magnetic stirrer at 37° to 40° C. An aqueous suspension containing semen in a modified semen extender consisting of a medium such as M-16 medium containing 5.56 mM fructose and 0.5% agarose and 0.25% sodium alginate is prepared. The suspension is dropped through a hypodermic needle to form droplets which fall into the solution. A capsular membrane forms almost instantaneously around the suspension droplet due to the cross-linking of the interfacial alginate molecules by $Ca^{2+}$ cations. The particles are equilibrated in a medium such as M-16 medium containing 0.05 M EDTA, which chelates the $Ca^{2+}$ resulting in liquefication of the Ca-alginate in the membrane. Finally, the particles consisting of solely of an agarose membrane are washed and stored in a medium such as M-16 medium. Optionally, the alginate is not removed from the particles.

FIGS. 3A and 3B illustrate the structure of particles which contain the alginate or solely the agarose, respectively.

EXAMPLE 9

Figure 5:
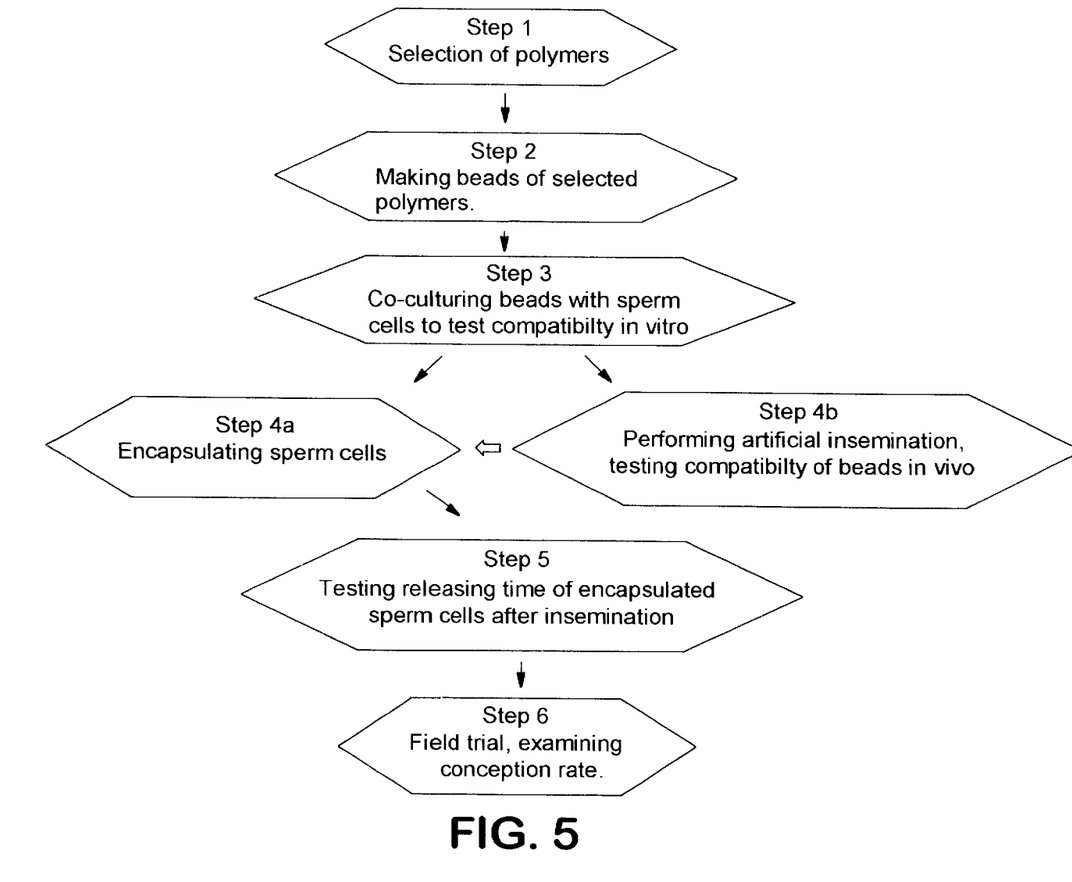
FIG. 5 is a flow diagram that illustrates the process for providing the encapsulated sperm of the present invention.

This example illustrates the approach to developing methods for encapsulating sperm which prolong the shelf-life and fertilizing ability of sperm. FIG. 5 provides a flow diagram that illustrates the approach.

Selection and Evaluation of Semen Extenders

Freshly ejaculated sperm are not fertile until they are capacitated. After capacitation, there is a window of opportunity when each sperm cell is fertile. Capacitated sperm, however, soon loose their fertilizing ability and die sooner than the non-capacitated sperm. When maintained in the precapacitated state, sperm cells can potentially survive for weeks. Thus to prolong semen shelf-life, the semen extender should be designed to maintain the sperm cells at the non-capacitated stage. Sperm cells stored in currently available semen extenders continue to capacitate (Lin, Ph.D. Dissertation, Michigan State University, East Lansing, Mich. (1996)). Results of studies in the applicants' laboratory have suggested a couple of potentially effective methods to modify the extender to slow down or prevent capacitation during storage (Lin et al. Biol. Reprod. 54, Suppl. 1 (1996)). The methods include the use of alternative energy sources that are likely to generate less reactive oxygen species (ROS) in sperm cells and addition of ROS sequesters. The redesign of the boar semen extender will apply the knowledge of other known factors in sperm preservation (Weitze, in Boar Semen Preservation II: Proceedings, Second International Conference on Boar Semen Preservation, Supplement to Reproduction in Domestic Animals. Eds: L. A. Johnson and K. F. Weitze, pp. 231–253 (1993), such as temperature and the calcium concentration (Pursel et al. J. Animal Sci. 37: 528–531 (1973); Cox et al. Mol. Reprod. Dev. 30: 135–147 (1991)).

The first task is to design a new semen extender with the above stated approaches that will decrease the rate of sperm capacitation when in storage. Boar semen is collected and diluted with trial semen extenders and stored at 64° F. or alternative temperatures. Several commercially available semen extenders are used to compare the effectiveness of the newly designed trial extenders. Sperm capacitation is assessed as percent of fresh, capacitated, and motile/non-motile sperm daily for up to three weeks after semen collection. Sperm capacitation is assessed by chlortetracycline fluorescent assay modified for boar sperm cells. Motion analysis is performed with a computer-assisted sperm analyzer (CellSoft manufactured by Cryo Resources, Montgomery, N.Y.). The motion parameters include percent of motile sperm, velocity (total distance traveled divided by total time the cell is tracked), linearity (the ratio of straight-line distance to actual track distance), amplitude of the lateral head (ALH), displacement (deviation of the sperm head from the mean trajectory), beat/cross frequency (the number of beats per second). One beat is defined as each time the sperm cell crosses the computer-calculated curval mean. The beat cross frequency and ALH displacement have been shown to be correlated to boar sperm fertilizing ability (Lin (1996)).

Selection and Evaluation of Polymers for Encapsulation

The female reproductive tract is an ideal environment to allow sperm capacitation to occur. A continuous supply of fresh and viable sperm over an extended period of time would increase the chance of fertilization to occur, especially when the time of ovulation predicted by standing heat is uncertain.

Different methods exist for encapsulating living cells, but the best techniques are those that do not subject the cells to undue physical, chemical, or thermal stresses, and result in the formation of a capsule with desired permeability to selected nutrients and wastes. The applicants have developed a mild and flexible technique for encapsulating various kinds of cells (U.S. Pat. No. 5,427,935). It is based on using a special membrane of ionotropic gel as the capsule template. This technique results in a capsule that consists of three key domains: the core, the capsule wall matrix, and the external barrier membrane.

A variety of hydrogel matrices are used to encapsulate the sperm cells. These capsules by design dissolve at different times in the female reproductive tract, thus, releasing fresh sperm over an extended period of time. The result of a single insemination mimics multiple inseminations by providing waves of fresh sperm cells.

The first task is to identify boar sperm compatible gel forming material in addition to calcium alginate and chitosan. To test for chemical compatibility, boar sperm is co-cultured with selected gel forming materials and then subjected to motion analysis and sperm capacitation assay as described above.

The second task is to test the mechanical condition of encapsulating the sperm and select particles of desirable size and thickness. The size of the particles is controlled between 0.5 mm to 3.5 mm, while the thickness of the membrane is controlled between 0.1 mm to 3 mm. Suitable sizes of particles and the strength and thickness of particle membranes is selected first by sham insemination of sows with particles without sperm.

The third task is to select for further feasibility studies encapsulating materials that dissolve after residing in the female reproductive tract for 24, 36, and 48 hours. Suitable gel forming conditions, such as temperature, pH, ionic strength of gel forming solution, and calcium concentration are tested and selected based upon the needs of the particular sperm cell type.

The fourth task is assessing the timing of capacitation to ensure that the staggered schedule is maintained after encapsulation and storage. The timing of capacitation is assessed by chlortetracycline fluorescent (CTC) assay. Shelf-life of encapsulated sperm is also examined by CTC assay and motion analysis.

By following the above approach, a new method of semen preservation is discovered which prolongs semen shelf-life in storage, increases pregnancy rates when semen is implanted into the uterus, and decreases the costs of artificial insemination management.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for artificial insemination of a mammal comprising:

(a) providing an admixture of capsules comprising a core containing sperm in a semen extender and a gel membrane formed of a gel forming polymer encapsulating the core, wherein the capsules have membranes of different thicknesses so that the capsules release the sperm in a mammal uterus at varying times during the fertile period of the mammal, said extender being free of glucose, xanthine oxidase, and $H_2O_2$, and comprising a carbohydrate source selected from the group consisting of fructose, fructose-6-phosphate, pyruvate, lactate, and mixtures thereof that provides an energy source for the sperm without facilitating capacitation of the sperm; and (b) introducing the admixture of capsules into the uterus of the mammal wherein the sperm in the capsules in the uterus is capacitated enabling the fertilization of an egg at the varying times during the fertile period of the mammal.

2. The method of claim 1 wherein glucose or precursors for a reactive oxygen species are delivered with the capsules containing the sperm into the uterus during the artificial insemination and wherein the glucose or oxygen species capacitate the sperm for the fertilization of the egg.

3. The method of claim 1 wherein particles containing glucose or precursors for reactive oxygen species are delivered with the capsules containing the sperm during the artificial insemination.

4. The method of claim 2 or 3 wherein the reactive oxygen species is produced by a mixture of xanthine and xanthine oxidase or $H_2O_2$.

5. The method of claim 1 wherein the gel forming polymer is a thermal gel selected from the group consisting of agarose, kappa-carrageenan, gelatin, agar, polyurethane-polyether polymers, and mixture thereof.

6. The method of claim 1 wherein the gel membrane has a thickness from 0.1 to 3.5 mm and containing therein sperm in a semen extender.

7. The method of claim 1 wherein the gel forming polymer contains a gel which dissolves in the uterus upon being warmed by and exposed to the uterus.

8. A method for artificial insemination of a mammal comprising:

(a) providing an admixture of solid beads formed of a gel forming polymer and comprising sperm in a semen extender dispersed throughout the beads, wherein the beads vary in chemical property and diameter so that the beads release the sperm in a mammal uterus at varying times during the fertile period of the mammal, said extender being free of glucose, xanthine oxidase, and $H_2O_2$, and comprising a carbohydrate source selected from the group consisting of fructose, fructose-6-phosphate, pyruvate, lactate, and mixtures thereof that provides an energy source for the sperm without facilitating capacitation of the sperm; and (b) introducing the admixture of beads into the uterus of the mammal wherein the sperm in the beads in the uterus is capacitated enabling the fertilization of an egg at the varying times during the fertile period of the mammal.

9. The method of claim 8 wherein glucose or precursors for a reactive oxygen species are delivered with the beads containing the sperm into the uterus during the artificial insemination and wherein the glucose or oxygen species capacitate the sperm for the fertilization of the egg.

10. The method of claim 8 wherein particles containing glucose or precursors for reactive oxygen species are delivered with the beads containing the sperm during the artificial insemination.

11. The method of claim 9 or 10 wherein the reactive oxygen species is produced by a mixture of xanthine and xanthine oxidase or $H_2O_2$.

12. The method of claim 8 wherein the gel forming polymer is a thermal gel selected from the group consisting of agarose, kappa-carrageenan, gelatin, agar, polyurethane-polyether polymers, and mixture thereof.

13. The method of claim 8 wherein the gel forming polymer contains a gel which dissolves in the uterus upon being warmed by and exposed to the uterus.

* * * * *